United States Patent [19]

Kambara et al.

[11] Patent Number: 5,015,766

[45] Date of Patent: May 14, 1991

[54] PREPARATION PROCESS OF ACRYLAMIDE

[75] Inventors: Yoshihiko Kambara, Takaishi; Itsuo Oonaka, Toyonaka; Koichi Asao; Kyoko Fukushima, both of Sakai, all of Japan

[73] Assignee: Mitsui Toatsu Chemicals, Incorporated, Tokyo, Japan

[21] Appl. No.: 284,727

[22] Filed: Dec. 15, 1988

[30] Foreign Application Priority Data

Dec. 16, 1987 [JP] Japan ................. 62-316020
Dec. 26, 1987 [JP] Japan ................. 62-330916

[51] Int. Cl.$^5$ ........................... C07C 231/06
[52] U.S. Cl. ................................. 564/127
[58] Field of Search ......................... 564/127

[56] References Cited

U.S. PATENT DOCUMENTS

| | | | |
|---|---|---|---|
| 3,767,706 | 10/1973 | Habermann | 260/561 N |
| 3,911,009 | 10/1975 | Yoshimura et al. | 260/561 |
| 4,000,195 | 12/1976 | Suarz et al. | 260/561 N |
| 4,056,565 | 11/1977 | Matsuda | 260/561 N |

OTHER PUBLICATIONS

Funabiki et al., "Liquid Phase Hydration Reaction of Acrylonitrile, etc.", *Spring Annual Conference of the Japan Chemical Society* (1986) (Presentation 1B40).
R. Mehrabian; Rapid Solidification Processing, (Principles and Technologies), Claitors' Publishing Div., (1987), 9.

*Primary Examiner*—Richard L. Raymond
*Assistant Examiner*—Peter G. O'Sullivan
*Attorney, Agent, or Firm*—Fisher, Christen & Sabol

[57] ABSTRACT

A molten Raney copper alloy containing copper and a metal selected from Al, Si and Zn as major components and, if necessary, specific metals as minor components is solidified at a cooling rate of not less than $1 \times 10^2$ K/sec by a rotary water atomizing process, water or gas atomizing process, single roll process or similar process. The Raney copper alloy thus obtained is leached to obtain a Raney copper catalyst. The resultant catalyst exhibits activity several times higher than that of conventional Raney copper catalysts in the reaction of acrylonitrile with water to give acrylamide.

6 Claims, 1 Drawing Sheet

PREPARATION PROCESS OF ACRYLAMIDE

BACKGROUND OF THE INVENTION

1. Field of the Invention

This invention relates to a process for the synthesis of acrylamide by reacting acrylonitrile with water in the presence of a Raney copper catalyst, and more particularly relates to remarkable enhancement of catalytic activity.

2. Description of the Prior Art

Acrylamide is a useful monomer employed for a wide field of applications in addition to be used for the preparation of acrylamide base polymers utilized for a paper reinforcing agent and a coagulating agent.

Acrylamide is now synthesized by reacting acrylonitrile which is now cheaply produced in industry with water in the presence of a solid catalyst.

Various copper base catalysts have been known as the solid catalyst used for the synthesis of acrylamide by reacting acrylonitrile with water. Raney copper catalyst is a typical one of such catalysts and disclosed in U.S. Pat. No. 3,767,706, U.S. Pat. No. 3,911,009 and U.S. Pat. No. 4,056,565.

The Raney copper catalyst is generally prepared by the following method. A molten alloy composed of copper and aluminum is poured into a mold, cooled and solidified, that is, cast. The resultant mass of alloy is then crushed to particles or powder with a jaw crusher or ball mill. Thereafter aluminum component is removed by leaching with sodium hydroxide and the like.

However, according to the information of the present inventors, the Raney copper catalyst obtained by the method does not exhibit satisfactorily high activity when the catalyst is used for the synthesis of acrylamide. Therefore the reaction temperature must be raised, whereby generation of impurities is increased and causes degradation of product quality.

Japanese Patent Publication No. 33612/1977 describes an example for intending to increase the activity by the addition of Sn, Fe, Co, Ru, Rh, Ir, Os or Pt to Raney copper catalyst. The addition of these metal components causes activity improvement to some extent. The resultant activity, however, is still much lower than satisfactory level.

Many examples are also found on the incorporation of secondary components to metallic copper catalysts other than Raney copper catalyst. In Japanese Patent Publication No. 43924/1978, copper salts are reduced by hypophosphite together with salts of metals such as Cr, V, Si, Fe, Ti and Zr, and subsequently decomposed by heat to give a metallic copper catalyst containing the secondary components. In Japanese Patent Publication No. 43927/1978, a metallic copper catalyst containing the secondary components is similarly obtained by reducing copper salts with boron hydrogen compounds under alkaline conditions together with salts of elements selected from the group IIa, IIb, IIIa, IIIb, IVa, IVb, Va, Vb, VIa, VIIa, and VIII elements in the periodic table. In Japanese Patent Publication No. 41241/1977 a metallic copper catalyst containing secondary components is obtained by reducing copper oxides in a hydrogen atmosphere together with oxides of metals such as Si, W, Hg, Zr, Fe, Ni, and Zn.

According to the information obtained by the present inventors, these metallic copper catalysts other than the Raney copper catalyst have much inferior activity to that of the Raney copper catalyst when the former catalysts are composed of copper alone. Some catalysts can be considerably enhanced their activity by the addition of other components for modifying these catalysts. Nevertheless, the resultant activity of these catalysts is slightly higher than that of the Raney copper catalyst.

SUMMARY OF THE INVENTION

An object of this invention is to provide a multi-element type Raney copper catalyst which is extremely active and useful for the preparation of acrylamide by reacting acrylonitrile with water.

Another object of this invention is to provide a method for improving the preparation of a Raney copper alloy which is effective for preparing the extremely active Raney copper catalyst and particularly a method for improving the catalytic activity by controlling a cooling rate in the solidification from a molten state.

A further object of this invention is to provide a suitable apparatus for the preparation of the above Raney copper catalyst.

The above-mentioned objects is achieved by providing the preparation process of acrylamide which comprises reacting acrylonitrile with water in the presence of a Raney copper catalyst obtained by solidifying a molten Raney copper alloy containing copper and at least one metal selected from Al, Si, and Zn as a major component at a cooling rate of not less than $1 \times 10^2$ K/sec, followed by leaching the solidified Raney copper alloy.

The above described Raney copper catalyst of this invention has the catalytic activity of 1.5–6 times as compared to that of previously known Raney copper catalysts.

1 is a rotary drum, 2 is a cooling liquid layer, 3 is a crucible, 4 is a heating coil, 5 is a fused alloy, 6 is a nozzle, and 7 is an argon gas inlet tube.

Figure 2:
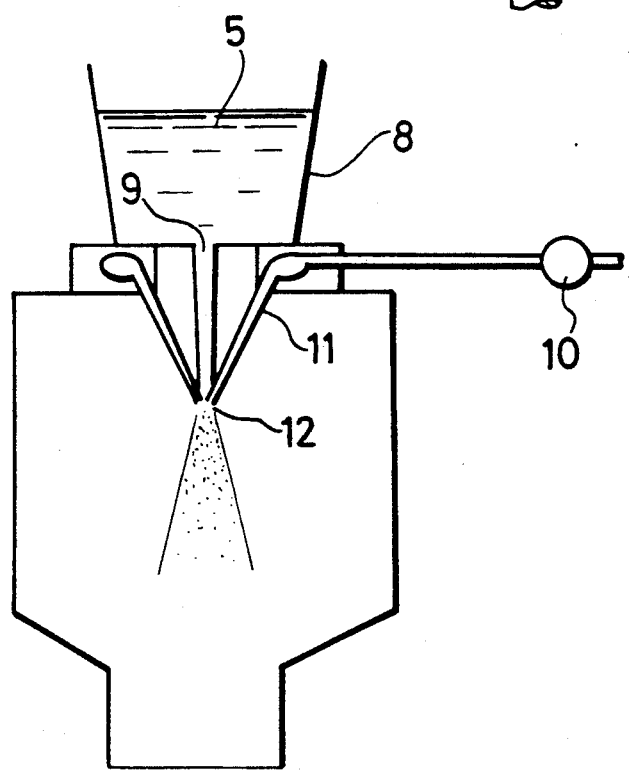

FIG. 2 is an example of an apparatus operated by a water or gas atomizing process. 8 is a tundish, 9 is a fused alloy feeding part, 10 is a high pressure pump, 11 is a cooling medium nozzle, 12 is contact part of the fused alloy and cooling medium.

Figure 3:
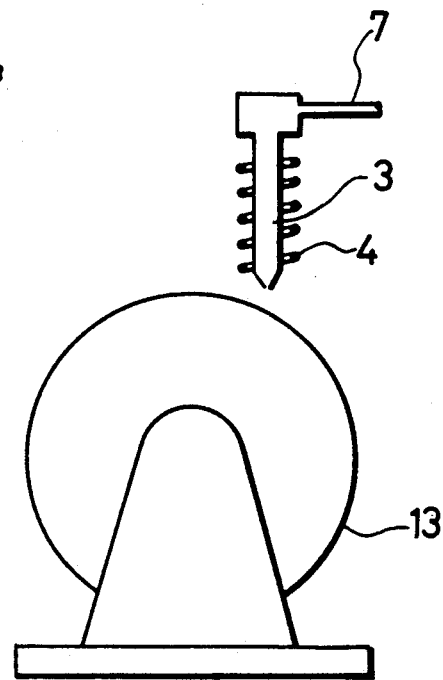

FIG. 3 is an example of an apparatus operated by a single roll process and 13 is a copper roller.

DETAILED DESCRIPTION OF THE INVENTION

The Raney copper catalyst used in the method of this invention is described, for example, in KAGAKUNO RYOIKI, 6, 733–740 (1952) (published from Nankodo Book Co.) and JIKKEN KAGAKU KOUZA, 17, 340–341 (1956) (published from Maruzen Book Co.). As described in these literatures, the Raney copper catalyst is defined as a metal catalyst obtained by preparing an alloy composed of alkali or acid soluble metals such as aluminum, silica, zinc, etc. and alkali or acid insoluble metals, and then leaching the resultant alloy. The metal composition primarily consists of copper in the metallic catalyst obtained after leaching.

The industrial reaction process of acrylonitrile and water in the presence of the Raney copper catalyst is usually carried out as described below. Water is used in about 0.5-10 times the amount of acrylonitrile. The reaction is conducted batchwise or continuously in the atmospheric pressure or under pressurized conditions by using the catalyst composed of a suspended bed or fixed bed. During the reaction, the reaction materials and the Raney copper catalyst are prevented under liquid phase from contact with oxygen or oxygen containing gases. The reaction temperature was about 90°-150° C. when previously known Raney copper catalyst was used. On the other hand, the Raney copper catalyst in the method of this invention has extremely high catalytic activity. Therefore equivalent production can be achieved even though the reaction temperature is about 5°-50° C. lower than that of the conventional method.

In preparing the material of the Raney copper catalyst used in the method of this invention, it is required to solidify the alloy in the molten state at a cooling rate of not less than $1 \times 10^2$ K/sec. Aluminum base alloys are generally prepared by pouring the fused alloy into a mold, cooling and solidifying at a cooling rate of about 0.1-10 K/sec. That is, the present invention requires a cooling rate at least about 10 times faster than that of molding method generally performed in industry. When the cooling rate is slow, the cooling rate can be obtained by reading the starting point and the finishing point of solidification on a constitutional diagram of the alloy and measuring the time required for temperature decrease between the above two points. Such a method, however, is difficult to carry out at a rapid cooling rate such as not less than $1 \times 10^2$ K/sec. Therefore, the cooling rate in the method of this invention is estimated by the following method.

Many alloys are known to perform so-called dendrite solidification (I. Oknaka, KIKAIKEI DAIGAKUKOUZA Series 24, Fusion Processing, page 43 (1987) (Published from Corona Co.). As to aluminum alloys, the alloy having a composition of 95.5% Al and 4.5% Cu is known to have the following relationship between so-called secondary dendrite arm spacing (μm) and the cooling rate of solidification (K/sec).

$$R = (50/d)^{2.455}$$

[R. Mehrabian; (Rapid Solidification Processing). (Principles and Technologies), Claitors' Publishing Div., (1987), 9]

That is, when the structure of the alloy having a composition of 95.5% Al and 4.5% Cu is observed the secondary dendrite arm spacing d of not more than 7.7 μm means the cooling rate R of not less than $1 \times 10^2$ K/sec.

The raw material alloy obtained at the cooling rate of $1 \times 10^2$ K/sec in the method of this invention means the alloy prepared by a method so that the secondary dendrite arm spacing d of not more than 7.7 μm is obtained when the alloy composed of 95.5% Al and 4.5% Cu is prepared by the same method and conditions as those for the preparation of the raw material alloy.

Dendrite cannot be observed at a rapid cooling rate, for example, a rate of not less than $1 \times 10^6$ K/sec. Of course, such condition is also in the scope of this invention.

As a practical process for preparing the alloy at a cooling rate of not less than $1 \times 10^2$ K/sec, it is preferred to prepare by applying so-called rapid solidification processing. The process is described, for example, in I. Oknaka, NISHIYAMA KINEN GIJUTSUKOUSA, Rapid Solidification Processing, page 238 (1986) (published from Japan Iron and Steel Association). When the alloy is prepared by applying water atomizing process, gas atomizing process, RSR atomizing process and rotary liquid atomizing process in particular, it is possible to obtain a cooling rate R of not less than $1 \times 10^2$ K/sec. At the same time, the product of alloy can be obtained in the form of powder and no further mechanical crushing is needed, thereby rationalization of production steps can be achieved.

The water atomizing process and gas atomizing process are, for example, such processes as illustrated in FIG. 2. There are various embodiments of these processes (See, for example, Japanese Laid-Open Patent No. 54508/1980 as to the water atomizing process) and a representative example will be described below.

In this process, the metal in the molten state, e.g., the fused alloy 5 is placed in a tundish 8 having an opening 9 at the bottom, fallen down through the opening 9 and brought into contact with high pressure gas or water at the point 12. Then the fused alloy is solidified rapidly and particulated. The gas and water are fed under high pressure with a high pressure pump 10 and passed through a cooling medium nozzle 11 to reach the point 12. The maximum cooling rate which can be realized by this process is approximately $1 \times 10^2 - 1 \times 10^5$ K/sec.

Figure 1:
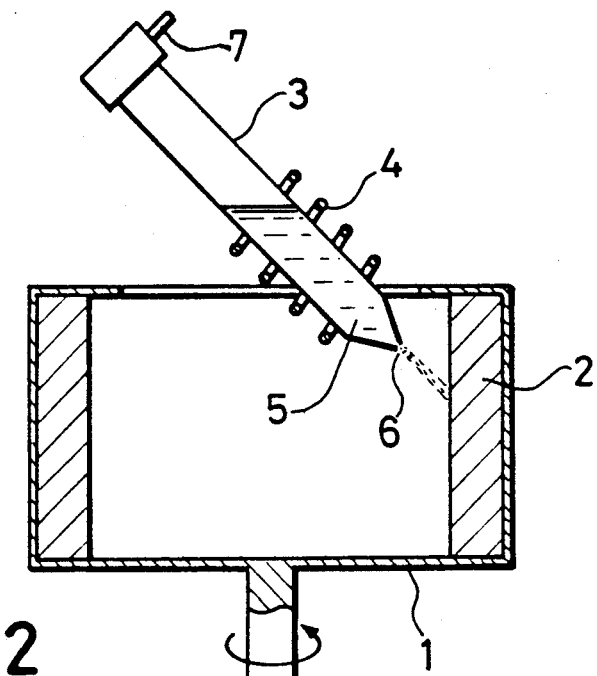
FIG. 1 is an example of an apparatus operated by a rotary liquid atomizing process. The apparatus is used for preparing the Raney copper alloy which is suitable for the preparation of the Raney copper catalyst employed in the preparation process of acrylamide of this invention.

The rotary liquid atomizing process is, for example, such process as illustrated in FIG. 1. A cooling liquid layer 2 is formed by centrifugal force in a rotary drum 1 rotating at a high speed. The fused alloy 5 is extruded by the pressure of argon gas 7 from a nozzle 6 located at the bottom of a crucible 3. The extruded alloy makes collision with the cooling liquid layer 2, quenched and particulated. The fused alloy 5 in the crucible 3 is maintained at a temperature by a heating coil 4. The rotary water atomizing process using water as the cooling liquid is described, for example, on the application to an alloy composed of 94.5% Al and 5.5% Cu in NIHON KINZOKU GAKUKAISHI, 47, No. 11, 1016-1021 (1983). According to the description, a cooling rate of $1 \times 10^3 - 5 \times 10^4$ K/sec is obtained under conditions of a circumferential velocity of rotating water of 33.5 m/sec, a crucible nozzle diameter of 0.23 mm and a injection pressure of fused alloy of 0.5 Kg/cm$^2$.

Rapid solidification processes other than the so-called atomizing process described above can of course be applied to the process of this invention. It is also possible in the method of this invention to prepare products in the form of a thin tape by applying single roll process, twin roll process and the like.

According to the presentation in the Spring Annual Conference of Japan Chemical Society (April 1, 1986) (Presentation No. 1B40; T. Funabiki et al, Liquid phase hydrating reaction of acrylonitrile by a Raney type catalyst prepared from Cu-Ti amorphous alloy), an amorphous alloy having a composition of $Cu_{67}Ti_{33}$ was prepared by the single roll process. The alloy was crushed with a vibration mill to particle size of less than 400 meshes, treated with 1N hydrofluoric acid and then subjected to Ti leaching. The catalytic activity of the Raney copper catalyst was estimated in the hydrating reaction of acrylonitrile. As a result, the Raney copper catalyst had higher catalytic activity than the catalyst obtained by hydrogenation of commercial copper powder. However, according to the information of the present inventors, the results thus obtained are much inferior to those of most general Raney copper catalysts obtained by leaching Cu-Al alloy with sodium hydroxide.

The catalyst component which is leached by acid or alkali in the method of this invention is Al, Si or Zn. The Raney copper catalyst of this invention contains a minor amount of other metallic components. When the alloy having such composition is prepared by the single roll process mentioned above, the alloy does not form an amorphous state. However, the Raney copper catalyst prepared by crushing and leaching the alloy has an extremely high activity as compared to the Raney copper catalysts provided by conventional methods.

The raw material alloy used for preparing the Raney copper catalyst of this invention contains at least one component selected from Al, Si and Zn as the alkali or acid soluble metallic component described above. The preparation of such component in the alloy is in the range of 25-75 weight %.

The catalytic activity of the Raney copper catalyst of the invention is much increased in the presence of a minor component, of at least one metal selected from Sc, Y, Ti, Zr, V, Nb, Ta, Cr, Mo, W, Mn, Tc, Re, Fe, Ru, Os, Co, Rh, Ir, Ni, Pd, Pt, Ag, Au, Zn, Cd, Ga, In, Tl, Si, Ce, Sn, Pb, Sb and Bi.

The proportion of the minor component in the raw material alloy is preferably in the range of 0.1-20 weight % and more preferably in the range of 0.1-10 weight %. The incorporation of other metallic components to Raney copper prepared by the conventional process has already been known in Japanese Patent Publication No. 33612/1977. However, the Raney copper catalyst obtained by the conventional process, that is, the process consisting of solidification in the mold and mechanical crushing, exhibits not so much increase in catalytic activity as compared with the Raney copper catalyst without minor component. Even though effect for enhancing activity is expected to additional components such as Ni as described in HYOMEN, 25, No. 11, 666 (1987), the activity of Ni added Raney copper catalyst is contrarily decreased when it is prepared by the conventional process.

On the other hand, by setting the cooling rate of the fused alloy at not less than $1.0 \times 10^2$ K/sec in the preparation of the raw material alloy, the Raney copper catalyst added with these metals can obtain an extremely large catalytic activity.

The Raney copper alloy obtained by rapidly solidifying the fused alloy according to the processes mentioned above can be easily leached to give the Raney copper catalyst by leaching methods such as ordinary alkali leaching. The Raney copper catalyst thus obtained can proceed with the reaction of acrylonitrile and water under usual reaction conditions, particularly at lower temperatures.

Preparation of alloy particles, leaching of the alloy and utility of the catalyst will hereinafter described by way of examples and comparative examples.

EXAMPLE 1

Preparation of alloy particles

An apparatus of so-called rotary water atomizing process having a rotating drum diameter of 215 mm was used as illustrated in Table 1. The drum was charged with 500 ml of water and rotated at the rate of 6000 rpm to form a water layer having a thickness of 13 mm. An alloy having a composition of 1% Ni-49.5% Cu-49.5% Al was retained in a crucible at 800° C. in a molten state and injected into the rotary water layer through a nozzle having a diameter of 0.7 mm by the argon gas pressure of 1.5 kg/cm$^2$G. As a result, the alloy particles thus obtained had a particle size passing through 32 mesh and a composition of 1% Ni-49.5% Cu-49.5% Al.

Estimation of cooling rate

The cooling rate in the preparation of the alloy particles was estimated by the following method.

An alloy having a composition of 95.5% Al-4.5% Cu was prepared under the same conditions as described above. Since the secondary dendrite arm spacing was 0.6-1.5 $\mu$m, the cooling rate was $5-10^3 \times 4 \times 10^4$ K/sec in the preparation process of the alloy.

Leaching of the alloy

The leaching is carried out by adding 20 g of thus obtained alloy particles having a composition of 1% Ni-49.5% Cu-49.5% Al to 150 g of a 20 wt. % aqueous sodium hydroxide solution at the temperature of 50° C. The Raney copper catalyst thus obtained was washed with previously deoxidized water until the pH of waste water lowers to 9 or less. As a result, 10 g of the Raney copper catalyst was obtained.

Evaluation of catalytic activity

In a 100 ml four necked flask, 8.5 g of previously deoxidized acrylonitrile, 55.0 g of previously deoxidized water and 7.0 g of the above obtained Raney copper catalyst were charged. The mixture was reacted in a nitrogen atmosphere at 70° C. for 2 hours. The yield of acrylamide was 64.3%.

COMPARATIVE EXAMPLE 1

A molten mixture of equal amount of copper and aluminum was poured into a cylindrical steel mold having a diameter of 4 cm and a depth of 10 cm and cooled to solidify the alloy. The constitutional diagram of this composition exhibited the starting point of solidification at 580° C. and the finishing point of solidification at 548° C. The time required for lowering the temperature between the above two points was about 4 seconds and thus the cooling rate was 8 K/sec.

The mass of alloy thus obtained was crushed with a ball mill to prepare particles passing through 42 mesh. The particles were leached and then the catalytic activity was evaluated by the same procedures as described in Example 1. The yield of acrylamide was 39.8%.

COMPARATIVE EXAMPLE 2

The same procedures as described in Comparative Example 1 were carried out except that the Raney copper catalyst was used in an amount of 4 times (24.0 g) in the evaluation of the catalytic activity. The yield of acrylamide was 65.3% in this test.

COMPARATIVE EXAMPLE 3

The alloy having the same composition as Example 1, that is, 1% Ni-49.5% Cu-49.5% Al, was prepared, leached and the catalytic activity was evaluated by the same procedures as described in Comparative Example 1. The yield of acrylamide was 30.5%.

EXAMPLE 2

An alloy composed of equal amount of copper and aluminum was prepared by the same procedures as described in Example 1. The alloy was leached and then the catalytic activity was evaluated by the same procedures as in Example 1.

As a result, the yield of acrylamide was 52.3%.

EXAMPLES 3–15

The apparatus of rotary water atomizing process was used as described in Example 1. Alloys were prepared so as to contain the metallic components illustrated in Table 1 in an amount of 1 wt. % or 5 wt. %. The alloys were leached and then the catalytic activity was evaluated by the same procedures as described in Example 1. The results are illustrated in Table 1.

COMPARATIVE EXAMPLES 4–9

Alloys were prepared by the same procedures as described in Comparative Example 3 so as to contain the metallic components in an amount of 1 wt. % or 5 wt. %. The alloys were leached and then the catalytic activity was evaluated by the same procedures as in Comparative Example 3. The results are illustrated in Table 1.

TABLE 1

| Example or Comparative Example | Additional metal Component | Amount (%) | Acrylamide yield (%) |
|---|---|---|---|
| Ex. 3 | Ni | 5 | 67.3 |
| Ex. 4 | Cr | 5 | 65.1 |
| Ex. 5 | Mn | 1 | 59.2 |
| Ex. 6 | Fe | 1 | 55.6 |
| Ex. 7 | Co | 1 | 60.3 |
| Ex. 8 | Ti | 1 | 80.3 |
| Ex. 9 | V | 1 | 78.4 |
| Ex. 10 | Sc | 1 | 75.2 |
| Ex. 11 | Zn | 5 | 73.1 |
| Ex. 12 | Sb | 1 | 63.1 |
| Ex. 13 | Sn | 1 | 62.4 |
| Ex. 14 | Ga | 1 | 59.3 |
| Ex. 15 | Nb + Mo | 1 + 1 | 73.3 |
| Comp. Ex. 4 | Ni | 5 | 23.1 |
| Comp. Ex. 5 | Cr | 5 | 18.4 |
| Comp. Ex. 6 | Mn | 1 | 42.2 |
| Comp. Ex. 7 | Fe | 1 | 39.7 |
| Comp. Ex. 8 | Co | 1 | 43.3 |
| Comp. Ex. 9 | Ti | 1 | 47.6 |

EXAMPLE 16

An apparatus of so-called gas atomizing process illustrated in FIG. 2 was used. The tundish provided with a nozzle located at the bottom and having a diameter of 1 mm, was charged with an alloy having a composition of 1% Ni–49.5% Cu–49.5% Al and maintain a molten state at 1000° C. The fused alloy was fallen through the nozzle, High-pressure air of 50 kg/cm$^2$G was injected to the stream of the fused alloy. The fused alloy was rapidly solidified to give alloy particles having particle size passing through 32 mesh and a composition of 1% Ni–49.5% Cu–49.5% Al. The estimated cooling rate was $1.8 \times 10^2$–$1.0 \times 10^3$ K/sec, because the secondary dendrite arm spacing of the alloy having a composition of 95.5% Al–4.5% Cu was 3–6 μm when prepared under the same conditions as above. The alloy particles containing 1% of Ni were leached and then the catalytic activity was evaluated by the same procedures as described in Example 1. As a result, the yield of acrylamide was 61.7%.

EXAMPLE 17

An apparatus of so-called single roll process was used. On a copper roller rotating at the rate of 5000 rpm and having a diameter of 12 cm, a molten alloy maintained at 1000° C. was fallen through a nozzle having a diameter of 0.7 mm by applying the argon gas pressure of 0.5 kg/cm$^2$G. The alloy thus obtained was in the form of a thin tape having a width of 2 mm and a thickness of 10–20 μm and had a composition of 1% Ni–49.5% Cu –49.5% Al. The resultant alloy was crushed in a ball mill to obtain particles passing through 400 mesh. The alloy particles were leached and then catalytic activity was evaluated. As a result, the yield of acrylamide was 65.3%.

In addition, a thin tape of the alloy having a composition of 95.5% Al–4.5% Cu was obtained by the same procedures as above. However, no distinct dendrite was observed and the cooling rate was estimated to be not less than $1 \times 10^6$ K/sec.

What is claimed is:

1. Process for the preparation of acrylamide which comprises reacting acrylonitrile with water in the presence of a Raney copper catalyst obtained by solidifying a molten raw material alloy comprising 15 to 75.0 weight percent of copper, 25 to 75 weight percent of Al as a major component and 0.1 to 10 weight percent of at least one metal selected from the group consisting of Sc, Ti, V, Nb, Cr, Mo, Mn, Fe, Co, Ni, Zn, Ga, Pd, Sn and Sb as a minor component at a cooling rate of $1 \times 10^2$ K/sec or more to produce a Raney copper alloy which is in a crystalline state, and followed by alkali leaching the Raney copper alloy.

2. The process of claim 1 wherein the cooling rate is $1 \times 10^2$ to $1 \times 10^7$ K/sec.

3. The process of claim 1 wherein the solidification is carried out by using one process selected from the group consisting of a rotary liquid atomizing process, a water atomizing process, a gas atomizing process and a single roll process.

4. The process of claim 1 wherein the solidification is carried out by using a rotary liquid atomizing process having a cooling rate of $1 \times 10^3$ to $5 \times 10^4$ K/sec.

5. The process of claim 1 wherein the solidification is carried out by using a water atomizing process having a cooling rate of $1 \times 10^2$ to $1 \times 10^5$ K/sec.

6. The process of claim 1 wherein the solidification is carried out by using a gas atomizing process having a cooling rate of $1 \times 10^2$ to $1 \times 10^4$ K/sec.

* * * * *